United States Patent [19]
Westenskow et al.

[11] Patent Number: 4,883,051
[45] Date of Patent: Nov. 28, 1989

[54] DISPOSABLE BREATHING SYSTEM AND COMPONENTS

[75] Inventors: Dwayne R. Westenskow, Salt Lake City; Fidel Silva, Sandy, both of Utah

[73] Assignee: Summa Vest, Inc., Salt Lake City, Utah

[21] Appl. No.: 158,949

[22] Filed: Feb. 18, 1988

[51] Int. Cl.$^4$ .................. A62B 7/00; A61M 16/00
[52] U.S. Cl. ................ 128/204.21; 128/204.25; 128/205.12; 128/205.13; 128/205.15; 128/205.17; 128/205.24
[58] Field of Search .............. 128/203.12, 203.14, 128/204.18, 204.21, 204.22, 204.23, 204.27, 205.11, 205.16, 205.17, 205.15, 909, 204.25, 204.26, 205.12, 205.14, 203.28, 205.13, 205.24

[56] References Cited
U.S. PATENT DOCUMENTS

| | | | |
|---|---|---|---|
| 1,737,575 | 12/1929 | Dražer | 128/203.28 |
| 2,847,001 | 8/1958 | Andreasen | 128/205.15 |
| 2,915,056 | 12/1959 | Lee | 128/203.14 |
| 3,467,092 | 9/1969 | Brid et al. | 128/204.25 |
| 3,537,450 | 11/1970 | Fox | 128/205.14 |
| 3,841,327 | 10/1974 | Hay | 128/204.29 |
| 3,844,280 | 10/1974 | Smythe | 128/205.13 |
| 3,890,967 | 6/1975 | Elan et al. | 128/205.17 |
| 3,901,230 | 8/1975 | Henkin | 128/205.17 |
| 3,903,881 | 9/1975 | Weigl | 128/204.25 |
| 3,916,890 | 11/1975 | Freeman | 128/205.14 |
| 3,921,628 | 11/1975 | Smythe et al. | 128/204.21 |
| 4,020,834 | 5/1977 | Bird | 128/204.25 |
| 4,044,763 | 8/1977 | Bird | 128/204.26 |
| 4,206,754 | 6/1980 | Cox et al. | 128/204.21 |
| 4,256,100 | 3/1981 | Levy et al. | 128/204.21 |
| 4,282,870 | 8/1981 | Porlier | 128/203.14 |
| 4,313,436 | 2/1982 | Schwanbom et al. | 128/203.12 |
| 4,340,044 | 7/1982 | Levy et al. | 128/204.21 |
| 4,453,543 | 6/1984 | Kohnke et al. | 128/205.17 |
| 4,508,117 | 4/1985 | Rodari | 128/204.21 |
| 4,637,385 | 1/1987 | Rusz | 128/205.15 |
| 4,702,240 | 10/1987 | Chaoui | 128/205.24 |

FOREIGN PATENT DOCUMENTS

| | | | |
|---|---|---|---|
| 1336301 | 7/1963 | France | 128/205.12 |
| 68886 | 5/1951 | Netherlands | 128/205.15 |
| 544343 | 4/1942 | United Kingdom | 128/203.28 |
| 2176313 | 12/1986 | United Kingdom | 128/203.12 |

OTHER PUBLICATIONS

Ohio Medical Products, "Operation Maintenance" Brochure for Ohio Anesthesia Ventilator.
Marquest Medical Products, Inc. brochure on Marquest Anesthesia Products.

*Primary Examiner*—Edgar S. Burr
*Assistant Examiner*—Kimberly L. Asher

[57] ABSTRACT

An anesthetic system and a transportation ventilation system include a breathing circuit which is isolatable from ventilator machines and anesthesia machines. The breathing circuit is connectable to the patient and includes a respiration bag within an actuator bag which is translucent and inelastic. The ventilation machine supplies signals so that the respiration bag collapses and expands within the actuator bag through a multi-port valve structure.

48 Claims, 12 Drawing Sheets

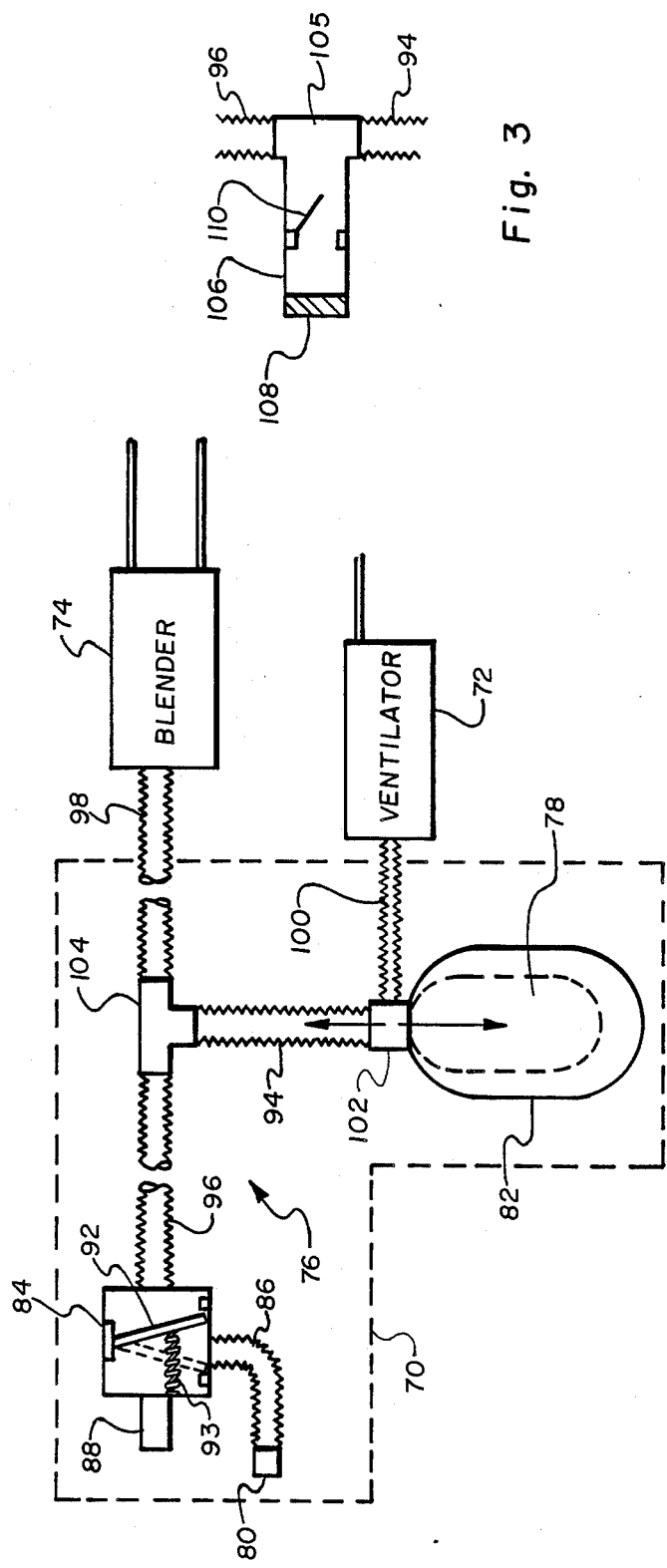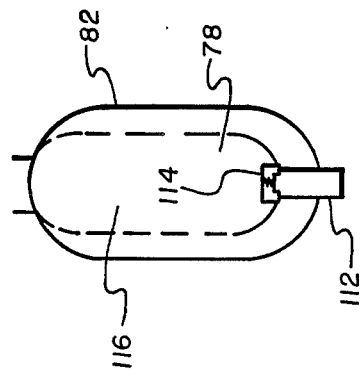

DISPOSABLE BREATHING SYSTEM AND COMPONENTS

BACKGROUND OF THE INVENTION

1. Field:

This invention relates to devices for supplying breathable gas to a patient. More particularly, this invention relates to disposable breathing systems and components thereof. Even more particularly, this invention relates in part to medical respiration or ventilation systems and anesthesia systems.

2. State of the Art:

Systems to ventilate a patient including anesthesia systems are in wide use today in the medical community. For example, a patient may be anesthetized such that mechanical means must be used to take over and ensure that the patient breaths. This enforced breathing or ventilation is today effected by interconnecting an anesthesia machine, a ventilation machine, and/or a breathing circuit to a patient, and more particularly to the external end of a endotracheal tube or mask which has been positioned in the patient's trachea.

In operation, the anesthesia machine supplies a mixture of breathable gas which typically includes an anesthetic mixed with air or oxygen. The ventilation machine operates to cause the anesthetic gas mixture and recycled respiratory gas to be supplied to the patient at a sufficient pressure to cause the gas mixture to pass through the breathing circuit and the endotracheal tube into the lungs of the patient. After inflating the lungs, the natural pressure of the expanded chest cavity will cause an expiration or a transfer of gas out of the patient back into the breathing circuit for reprocessing or recycling, all on a periodic basis which is typically set to accommodate the individual patient's breathing rate or respiration rate.

Ventilation systems that are in use typically include a ventilation device and/or a breathing circuit for interconnection to the patient in order to assist or to take over the breathing function for the patient. Such systems may be used during transport of the patient between two points for medical treatment or in an emergency situation where a patient has stopped breathing for whatever reason, and in other circumstances where the patient requires assistance in breathing for a limited or even an extended period of time based on a medical condition. The Ohio 7000 is one such ventilator machine. It is presently sold by Ohio Medical Products with offices at 3030 Airco Drive, Madison, Wis. 53707. The Ohio 7000 anesthesia ventilator may be used to control ventilation of a patient in a variety of circumstances including anesthesia. Breathing circuits, and more particularly disposable anesthesia circuits, may be purchased for interconnection with anesthesia machines and ventilation machines. A disposable breathing circuit may be purchased from Marquest Medical Products, Inc., of Englewood, Colo. 80112.

Anesthesia systems and ventilation systems are well known in the art. For example, U.S. Pat. No. 3,841,327 (Hay) discloses an anesthesia ventilator apparatus similar to that presently being sold as the Ohio 7000 ventilator apparatus. U.S. Pat. No. 3,903,881 (Wiegl) discloses a respirator system for use in ventilating a patient. U.S. Pat. No. 3,844,280 (Smythe); U.S. Pat. No. 3,921,628 (Smythe et al.); U.S. Pat. No. 3,916,890 (Freeman); and U.S. Pat. No. 3,467,092 (Bird et al.) all disclose ventilation and anesthesia apparatus or systems for use in ventilating the patient.

Many ventilation systems today employ a variety of components including a reservoir or respiration bag which is used continuously or from one patient to the next. That is, many of the components of a ventilation system are not disposable or simply not disposed of.

It is recognized within the medical community that some number of different diseases may be communicated from person to person through the oral transmission of organisms. Today there is increasing attention to AIDS prevention or control. The substantial unknowns associated with AIDS has precipitated increasing concern that infectious AIDS organisms may be communicated from one patient having the disease to the next by successive use of similar ventilation or anesthesia systems because the systems are not disposable and have not been thoroughly cleaned even though substantial effort may have been devoted to cleaning the systems.

In effect, an anesthesia system and a ventilation or transportation ventilation system is needed in which the breathing circuits can be disposable, while expensive anesthesia machines and ventilation machines are themselves isolated from the breathing circuit and the patient.

SUMMARY OF THE INVENTION

An anesthesia system includes an anesthesia machine connected to an external source of gas to receive and supply a preselected mixture of breathable gas. A disposable breathing circuit is interconnected between the anesthesia machine and a patient. The disposable breathing circuit has a connector for connection to the anesthesia machine and a connector for connection to the patient. The circuit also has a reservoir connected to receive, store and supply the preselected mixture of gas and also to store respiratory gas and to supply respiratory gas to and receive it from the patient. Tube means interconnect the reservoir with the first and second connector means. An actuator is positioned operatively proximate to the reservoir to urge the reservoir means between a collapsed first position, in which the anesthesia gas and respiratory gas therewithin are supplied to the patient via the tube means, and an expanded second position, in which the respiratory gas is expelled from the patient via the tube means to the reservoir means. The anesthesia system also includes a ventilation machine means which generates inspiration signals and expiration signals in accordance with a preselected pattern. The ventilation machine means is removably connected to the actuator means to supply the inspiration signals and expiration signals thereto to urge the reservoir means between the first and second positions respectively.

In a preferred arrangement, the reservoir means is a respiration bag which is formed to collapse upon receipt of the inspiration signals and expand upon receipt of the expiration signals. Preferably, the actuator means includes an actuation container formed of substantially inelastic material with the respiration bag sealedly positioned therewithin The inspiration signals are preferably a positive pressure, and the expiration signals are the release of positive pressure The inspiration and expiration signals operate to urge the respiration bag to the collapsed first position from the expanded second position. The actuation container is alternately a rigid container with sides, one of which is manually and slidably moveable toward the interior of the rigid container to contact and collapse the respiration bag.

In a preferred arrangement, the actuator means includes an actuator bag which is formed of a gas impermeable and substantially inelastic flexible material to be manually collapsible about the respiration bag.

In one embodiment, the disposable breathing circuit further includes absorber means which is interconnected within the tube means to receive the respiratory gas from the patient and to supply the respiratory gas to the respiration bag. The absorber means functions to remove carbon dioxide from the respiratory gas.

A transport ventilation system similar to the anesthesia system includes a disposable breathing circuit which has supply means selectively adapted to supply a breathable gas from an external source. A connector interconnects the circuit to the patient to supply and receive respiratory gas. A reservoir means is connected to receive, store and supply the respiratory gas. Tube means interconnects the connector means and the reservoir to communicate gas therebetween. An exhaust means is interconnected in the tube means to exhaust respiratory gas from the patient. An actuator means is positioned proximate the reservoir means similar to the actuator means in the anesthesia circuit. The transportation ventilation system also includes a ventilation machine means similar to the ventilation means used in the anesthesia system.

In preferred embodiments of the anesthesia system and the transportation system, a valve interconnects the reservoir means to the breathing circuit and to the ventilation machine means. The valve has a plurality of ports for interconnecting the reservoir means and the actuator means thereto. The ports and channels communicate therebetween so that signals may be communicated between a preferred actuator bag and respiration bag to collapse and expand the respiration bag. In other preferred embodiments, the valve has pressure sensors proximately positioned to sense the flow of gas in and out of the respiration bag.

BRIEF DESCRIPTION OF THE DRAWINGS

In the drawings, which illustrate the best mode presently contemplated for carrying out the invention:

FIG. 2 is a simplified diagram of a transportation ventilation system of the instant invention;

FIG. 3 is a supply inlet valve for use in a transportation ventilation system of the instant invention;

FIG. 4 is a representation of an alternate supply means for use in a transportation ventilation system of the instant invention;

DESCRIPTION OF THE ILLUSTRATED EMBODIMENTS

Figure 1:
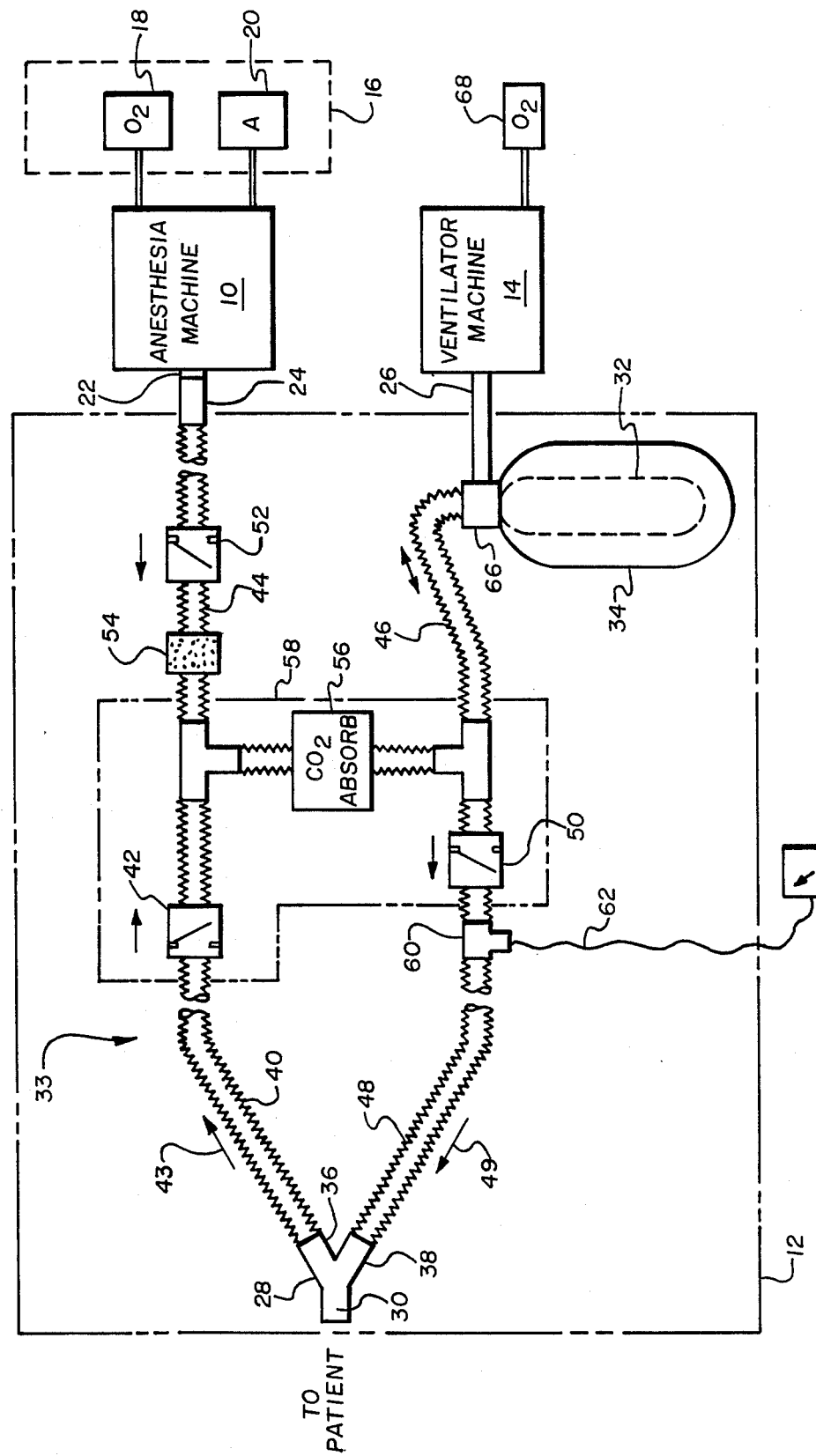
FIG. 1 is a simplified diagram illustrating an anesthesia system of the instant invention.

An anesthesia system of the instant invention is generally illustrated in FIG. 1. It includes an anesthesia machine 10, a disposable breathing circuit 12, and a ventilator machine 14.

The anesthesia machine 10 may be any one of several anesthesia machines readily available on the market. It is a machine that specifically receives a breathable gas from an external source such as source 16 which here includes a source of oxygen 18 as well as a source of anesthesia gas 20 such as halothane or isoflorane. Other suitable anesthesia gases may be used as desired by the user. The anesthesia machine 10 receives the breathable gas from the source 16, and more particularly the oxygen from source 18 and the anesthesia gas from source 20, and mixes them in accordance with controls as set by the user. That is, the user is provided with controls on the anesthesia machine to mix the oxygen and anesthesia gas to produce the desired preselected mixture of gas to be supplied at the output 22 of the anesthesia machine, all in a manner well known to those skilled in the art. The anesthesia machine 10 is connected at its output 22 to a connector 24 which interconnects the anesthesia machine 10 to the disposable breathing circuit 12 as more fully discussed hereinafter.

The anesthesia machine 10 is typically sized to supply a variable rate of preselected mixture of gas or anesthesia gas. Although a wide range of flow rates may be used at a wide range of pressures, all selectable by the user, it is typical to supply the preselected mixture of anesthesia gas at a rate from about 1 to about 5 liters per minute at a pressure selected so that gas will continuously flow out of the anesthesia machine and into the disposable breathing circuit 12 to which the anesthesia machine has been removably connected via connector 24.

The ventilator machine 14 is here shown to be connected to the disposable breathing circuit 12 via line or tube 26 as more fully discussed hereinafter. The disposable breathing circuit 12 has connector means which is here shown as connector 24 for connection and preferably removable connection to the anesthesia machine 10 to receive the preselected mixture of gas therefrom.

A second connector means here shown as connector 28 is provided for connection to the patient to receive and supply respiratory gas. More particularly, one leg or the first leg 30 of the connector 28 is sized to adapt to the patient and typically the endotracheal tube inserted in the patient's trachea. For inspiration, respiratory gas is supplied to the patient under pressure which causes the patient's chest cavity to expand. Upon cessation of the inspiration flow and the lowering of the pressure, the expanded chest exerts an inward force to squeeze the lungs and in turn cause expiration or discharge of the supply of respiratory gas outward from the patient. In a typical situation in which an anesthetic is being supplied, the leg 30 of connector 28 is adapted either to another tube for further connection to an endotracheal tube or directly to an endotracheal tube as circumstances warrant and as desired by the user.

The disposable breathing circuit 12 of FIG. 1 includes a reservoir means 32 which is interconnected to receive, store and supply the preselected mixture of gas coming into the disposable breathing circuit 12 from the anesthesia machine 10 and the respiratory gas being supplied to and received from the patient. Even though the circuit 12 shown is described herein as disposable, those skilled in the art will recognize that it may be reused and also constructed of materials intended for reuse.

The disposable breathing circuit 12 is shown in FIG. 1 to include tube means such as tubing 33 which is interconnected between the first connector means such as connector 24 and a second connector means such as connector 28 both to the reservoir means 32 such as a respiration bag to communicate respiratory gas from the patient to the reservoir means upon expiration from the patient and from the reservoir means to the patient upon inspiration of gas to the patient. The tube means at the same time is connected to communicate the preselected mixture of gas from the anesthesia machine means to the reservoir means.

The disposable breathing circuit 12 also includes an actuator means which is here shown to be an actuator bag 34. The actuator means is positioned operatively proximate to the reservoir means such as reservoir 2 to urge the reservoir means between a first position in which a preselected mixture of gas and the respiratory gas therewithin are expelled and supplied from the reservoir 32 to the patient via the tube means and a second position in which the respiratory gas is expelled from the patient and supplied via the tube means to the reservoir 32 and also to receive a preselected mixture of gas via the tube means from the anesthesia machine means.

As noted, the actuator means causes the reservoir means to operate between a first position and a second position. The ventilation machine means generates inspiration signals and expiration signals in accordance with a preselected pattern as selected by the user and more fully described hereinafter. The ventilation machine supplies the inspiration signals and the expiration signals to the actuator means to thereby urge the reservoir means between the first and second positions respectively. The illustrated actuator bag 34 is desirably made of material selected to be collapsible about the reservoir means 32, which is a respiration bag, but inelastic so that the inspiration/ expiration signals will cause the bag to operate between the first and second position. The bag 34 may also be manipulated by hand to manually ventilate. Further, the bag 34 is desirably translucent so the user can observe operation of the respiration bag.

Referring specifically to the disposable breathing circuit 12 of FIG. 1, it can be seen that in addition to the first leg 30 for connection to the patient, the connector 28 has a second leg 36 and a third leg 38. The tube means is a network of tubing 33 and is here shown to have a first branch 40. The first branch 40 receives respiratory gas from the patient and supplies it to the reservoir 32.

In the preferred arrangement, the first branch 40 includes a first one-way valve 42 which is positioned in the branch 40 so that respiratory gas may proceed outwardly in the direction of the arrow 43 through the first one-way valve 42 toward the reservoir 32. However, the valve 42 inhibits the flow of gas toward the patient through the first branch 40. The valve 42 may be of any of several which function as a check valve with a closed position to inhibit flow upstream and an open position which permits flow downstream.

The tubing 33 includes a second branch 44 which is interconnected between the anesthesia machine 10 and the first branch 40. More particularly, the second branch 44 interconnects into the first branch 40 downstream of the first one-way valve 42. Thus, the continuous supply of the preselected mixture of gas from the anesthesia machine 10 to the disposable breathing circuit 12 proceeds from the anesthesia machine 10 and into the first branch 40 but downstream of the first one-way valve 42.

The tubing 33 also includes a third branch 46 and a fourth branch 48. The fourth branch 48 supplies respiratory gas to the patient in the direction of arrow 49 from the reservoir 32. The fourth branch 48 includes another one-way valve 50 which is positioned to permit respiratory gas to flow in the direction 49 towards the patient but which inhibits the flow of respiratory gas outwardly from the patient. One-way valve 50 is similar in construction and function to valve 42. By virtue of the one-way valves 42 and 50, it can be seen that as the patient is ventilated or ventilates, respiratory gas proceeds out from the patient through the valve 42 toward the reservoir 32 upon expiration and in from the reservoir 32 through the one-way valve 50 to the patient via the fourth leg 48 upon inspiration.

To specifically prevent and guard against the transmission of respiratory gas into the anesthesia machine 10, the machine 10 is operated so that the preselected mixture of gas flows continuously to further protect the anesthesia machine 10. Another one-way valve 52 may be provided in the second branch 44 to inhibit the flow of respiratory gas into the anesthesia machine 10. Desirably, the output of the anesthesia machine 10 may also pass through a filter 54 to filter the gas if desired.

The disposable breathing circuit 12 is here shown to include an absorber means which is here shown to be a carbon dioxide ($CO_2$) absorber 56. The absorber 56 includes a compound which will absorb carbon dioxide gas. The respiratory gas from first branch 40 is connected to flow through the $CO_2$ absorber 56 to remove carbon dioxide therefrom, to in effect purify the respiratory gas for reuse by the patient. Optionally, the $CO_2$ absorber 56 may be part of a disposable canister 58 which includes portions of the first branch 40, the fourth branch 48, the third branch 46, and the second branch 44 as well as one-way valves 42 and 50.

It can also be seen in FIG. 1 that the fourth branch 48 has an oxygen detector 60 interconnected therein for sensing the oxygen concentration of the respiratory gas proceeding therethrough in the direction 49 to the patient. The detector 60 may be any one of a number of different well-known oxygen detectors. Here the preferred detector is a polarographic oxygen detector which senses the oxygen molecules and sends an electrical signal reflective of their presence and in turn the oxygen concentration via conductor 62 to an indicator 64 positioned remotely for observation by the user.

It can be seen in FIG. 1 that the ventilator machine 14 is connected via the tube or connector 26 to the disposable breathing circuit 12, and more particularly to a valve 66 which interconnects the ventilator machine 14 to the actuator bag 34 and at the same time interconnects the third branch 46 to the reservoir bag 32. Thus, the ventilator machine 14 supplies inspiration and expiration signals to the actuator means such as actuator container or actuator bag 34 to cause the reservoir means to collapse and expand between the first position and second position as hereinbefore stated. The ventilator machine 14 may be operated by gas pressure and more particularly by an external source of gas which is here shown to be a source of oxygen 68. However, it should be understood that any suitable compressed gas could be used such as nitrogen or compressed air.

Referring now to FIG. 2, the transport ventilation system of the instant invention includes a disposable breathing circuit 70 interconnected with a ventilator machine means, and more particularly a ventilator machine 72 similar to the ventilator machine 14 of FIG. 1 and is more fully described hereinafter. The disposable circuit 70 includes supply means selectively adapted to the tube means such as tubing 76 and to a reservoir means such as respiration bag 78, to supply a breathable gas to the circuit 70 from an external source. FIGS. 3 and 4 illustrate alternative embodiments of supply means which are more fully discussed hereinafter. The supply means shown in FIG. 2 is a blender machine 74 which supplies an appropriate blend of breathable gases from external sources such as sources of air and oxygen.

The disposable breathing circuit 70 includes a connector 80 for connection to a patient to supply and receive respiratory gas therefrom. The breathing circuit 70 includes tube means 76 to interconnect the connector 80 with the reservoir means. The circuit 70 also includes actuator means which is here an actuator container or actuator bag 82 which is positioned operatively proximate to the reservoir means such as respiration bag 78 to urge the respiration bag 78 to a collapsed first position, in which respiratory gas is supplied from the bag 78 directly to the patient via the tube means 76, and from an expanded second position to exhaust the respiratory gas from the patient via the connector means 80.

In the specific embodiment illustrated in FIG. 2, the connector 80 is connected to a two-way valve 84 which here functions as exhaust means and is here depicted to show one position in phantom and the other position in solid. In the solid or first position, respiratory gas proceeds from the patient through tube segment 86 and through the two-way valve 84 to an exhaust port 88 whereby the respiratory gas is exhausted to the atmosphere. Upon inspiration, the pressure in the segment 96 increases causing valve disk 92 to move against the bias of spring 93 into the second or phantom position, whereby respiratory gas proceeds from the respiration bag 78 via the tubing 76, and more particularly tube segments 94 and 96 through the two-way valve 84 and the tube segment 86 to the patient via connector 80. At the same time, breathable gas is proceeding into the tube segments 94 and 96 from the blender 74 via tube segment 98. Thus, the transportation ventilation system of FIG. 2 operates in a manner such that the patient continuously receives a fresh supply of respiratory gas from the blender 74 and the respiration bag 78. Since the blender 74 supplies breathable gas at a constant or regulated flow and in turn at a pressure, the spring 93 of valve 84 is sized to hold the disk 92 in the first (solid) position during expiration.

As seen in FIG. 2, the ventilator machine 72 is interconnected to the disposable circuit 70 via connector or tube 100 to a valve 102 to supply inspiration and expiration signals via the valve 102 to the actuator means, and more particularly to the actuating container or actuator bag 82. At the same time, the valve 102 receives from and supplies respiratory gas to the respiratory bag 78.

Referring to FIG. 3, an alternate embodiment is shown in which the "T" connector 104 (FIG. 2) is eliminated and replaced so that the gas proceeds between segment 96 and segment 94 via an in-line connector 105 which also has an inlet one-way valve 106 unitarily formed therewith with a filter 108 positioned to remove particulate matter from the atmosphere. When inspiration is completed, air proceeds inwardly through the valve 106 in the open position as illustrated in FIG. 3 to supply air to the respiration bag 78. However, it should be understood that the flow of air will principally be from the valve 106 through leg 94 to the respiration bag 78 during the period of expiration in which respiratory gas is being exhausted via tube segment 86, via two way valve 84 to the atmosphere via exhaust 88.

FIG. 4 shows an alternate arrangement of an actuator bag 82 and a respiration bag 78 of FIG. 2 configured with an inlet 112 positioned to pass through the actuator bag into the respiratory bag 78. A spring loaded poppet valve 114 is positioned within the respiratory bag 78 so that when the bag 78 is collapsed, the poppet valve 114 opens to allow air to proceed from outside the actuator bag 82 through the inlet 112 and the poppet valve 114 to the interior 116 of the respiration bag 78.

Figure 5:
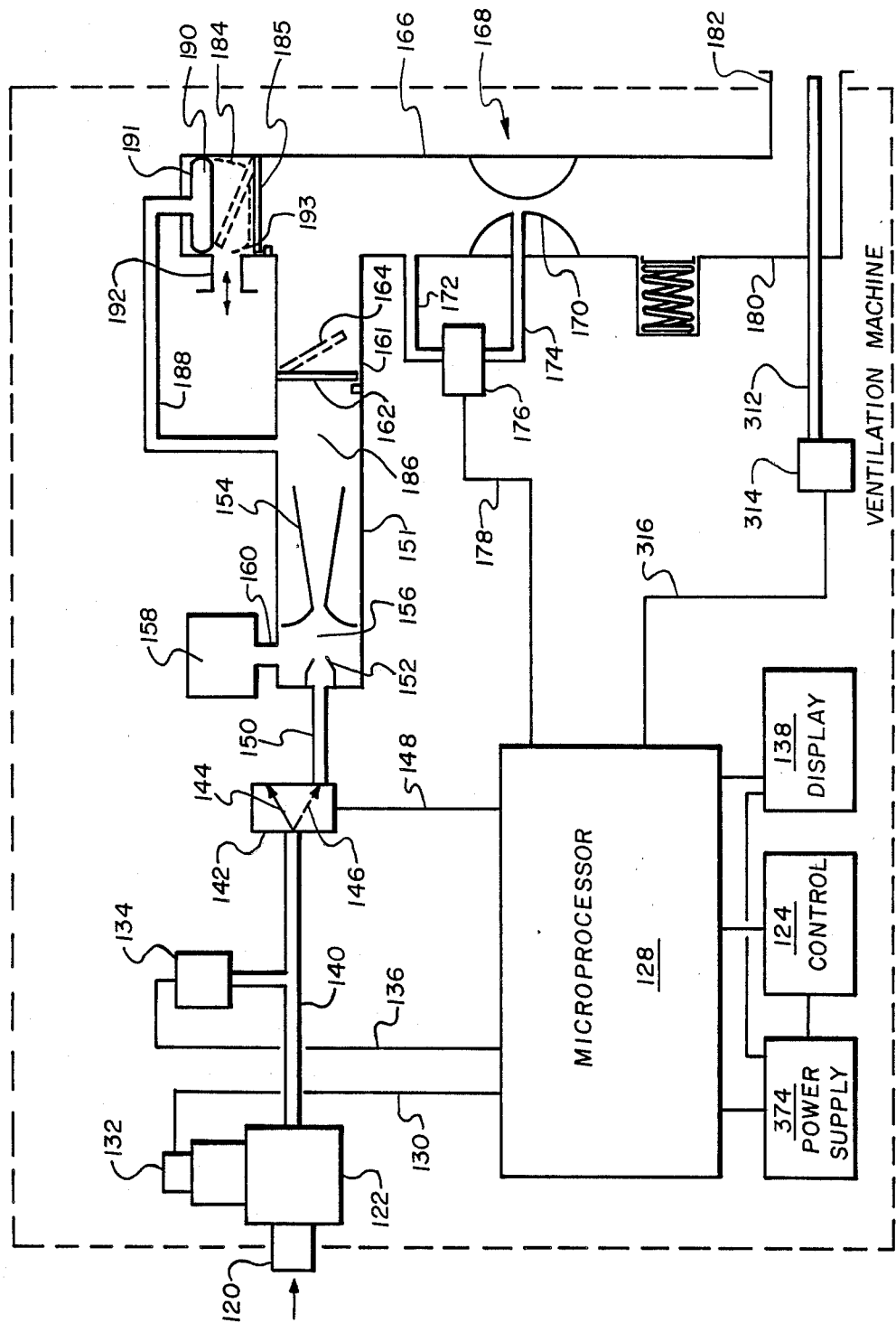
FIG. 5 is a simplified diagram of a ventilation machine of the instant invention.
Figure 8:
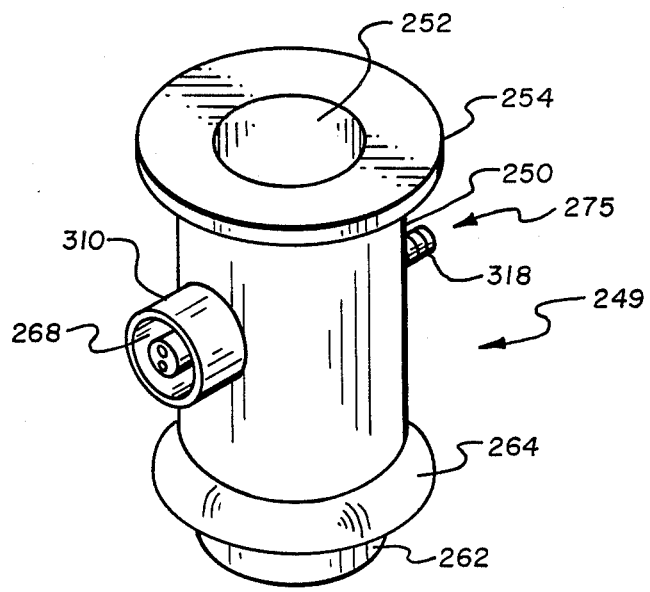
FIG. 8 is a perspective representation of the valve of FIG. 7.
Figure 9:
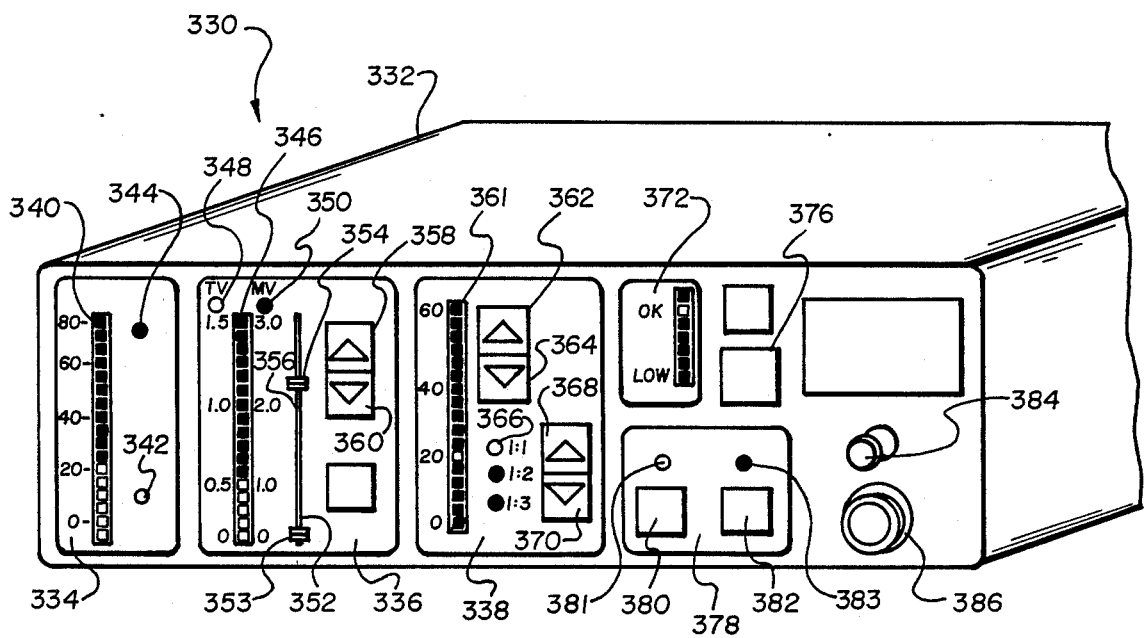
FIG. 9 is a perspective partial illustration of the chassis and control means of a ventilation machine of the instant invention.

Referring now to FIG. 5, a ventilation machine is graphically depicted with the various components thereof positioned within the chassis which is illustrated in FIGS. 8 and 9 hereinafter discussed. In FIG. 5, a gas under pressure is received from an external source via connector 120. As noted in FIG. 1, the external source may be a source of pressurized oxygen such as source 68 (FIG. 1). It may also be a source of compressed gas suitable for use such as compressed air or compressed nitrogen. Most logically, cost considerations would suggest the use of compressed air or another readily available, cheap gas otherwise not hazardous.

The gas from one source proceeds through the connector 120 to a pressure regulator 122. The regulator 122 is adjustable. That is, the regulator 122 is of the type to regulate the pressure downstream to be at or below the upstream pressure as selected by the user. Here the user may select the desired pressure by manipulation of an appropriate control on a control panel 124, to generate a control signal which is in turn processed by a microprocessor 128. The microprocessor 128 then supplies a signal via conductor 130 to a stepper motor 132, which in turn rotates or operates mechanical components of the regulator valve 122 to adjust the downstream pressure as desired.

The pressure downstream is detected by transducer 134, which in turn supplies an electrical signal reflective thereof via conductor 136 to the microprocessor 128 for processing and for appropriate display on display panel 138 as more fully discussed hereinafter.

The regulated air output of the regulator valve 122 is supplied via an appropriate tube 140 to a solenoid valve 142 which operates between a first closed position illustrated in solid at 144 and a second open position illustrated in dotted line 146. The valve 142 is operated between the first position 144 and the second position 146 by an electrical solenoid which is controlled via conductor 148 by the microprocessor 128 in accordance with signals received from the control panel 124 as more fully discussed hereinafter. The regulated air under pressure proceeds from the tube 140 through the valve 142 in the second position 146 and a second tube 150 through a mixing means such as the venturi structure 151. That is, the regulated air supplied via tube 150 enters the venturi structure 151 via a nozzle 152 which directs the regulated air at an increased velocity into a venturi tube 154. The low pressure thereby created by the nozzle 152 immediately downstream thereof, at 156, causes air to be sucked in through muffler 158 and-channel 160. The mixture passes through the venturi structure 151 into a check valve structure, and more particularly one-way valve 161. The valve 161 is shown in a closed position 162 in solid and in an open position 164 in dotted or phantom. With air proceeding through the solenoid valve 142 and the tube 150 through nozzle 152 and the venturi 154, the one-way valve 161 opens to the dotted or phantom position 164 allowing a gas mixture to proceed through additional tubing 166 to a flow measuring venturi structure 168.

The flow measuring venturi structure 168 is comprised of a constriction which may be in the form a venturi 170 or a simple orifice with pressure sensing apertures upstream 172 and downstream 174. The pressure sensed upstream 172 and downstream 174 is measured by differential pressure transducer 176 which communicates a signal reflective of the differential pressure, and in turn the flow rate via conductor 178 to the microprocessor 128 for processing and display on the display panel 138.

The gas mixture proceeds beyond the flow meter structure 168 through the tubing 180 to an output connector 182 for connection to actuator means such as actuator bag or container 82 (FIG. 2) and actuator bag or container 34 (FIG. 1) or to a breathing circuit.

The ventilation machine of FIG. 5 also includes a power supply which may be a battery pack 374 to supply power to the microprocessor and to other electrical components of the ventilation machine as desired.

The ventilation machine also includes an exhalation valve structure which is here illustrated to be comprised of a one-way valve 184 shown in a closed position 185. That is, with the solenoid valve 142 in the second position 146, regulated air passes into the venturi structure 151 (and more particularly the venturi 154). Thus, gas under pressure exists in region 186 which in turn is communicated via tubing 188 to an expandable mushroom valve 190. The valve 190 is shown in a collapsed position in solid 191 and in a expanded position 193 in dotted line. In the expanded position 193, it holds the one-way valve 184 in the closed position 185. When the solenoid valve 142 moves to the first position 144, air pressure or gas under pressure may leak outward through the muffler or filter 158. Thus, the mushroom 190 can collapse to the solid position as shown in FIG. 5. Thus, air proceeding upstream toward the venturi 154 will cause the first one-way valve 161 to the closed position 162 and the second one-way valve 184 to proceed to the open position shown in dotted lines in FIG. 5 so that air may proceed through an exhaust port 192 to the atmosphere.

Figure 6:
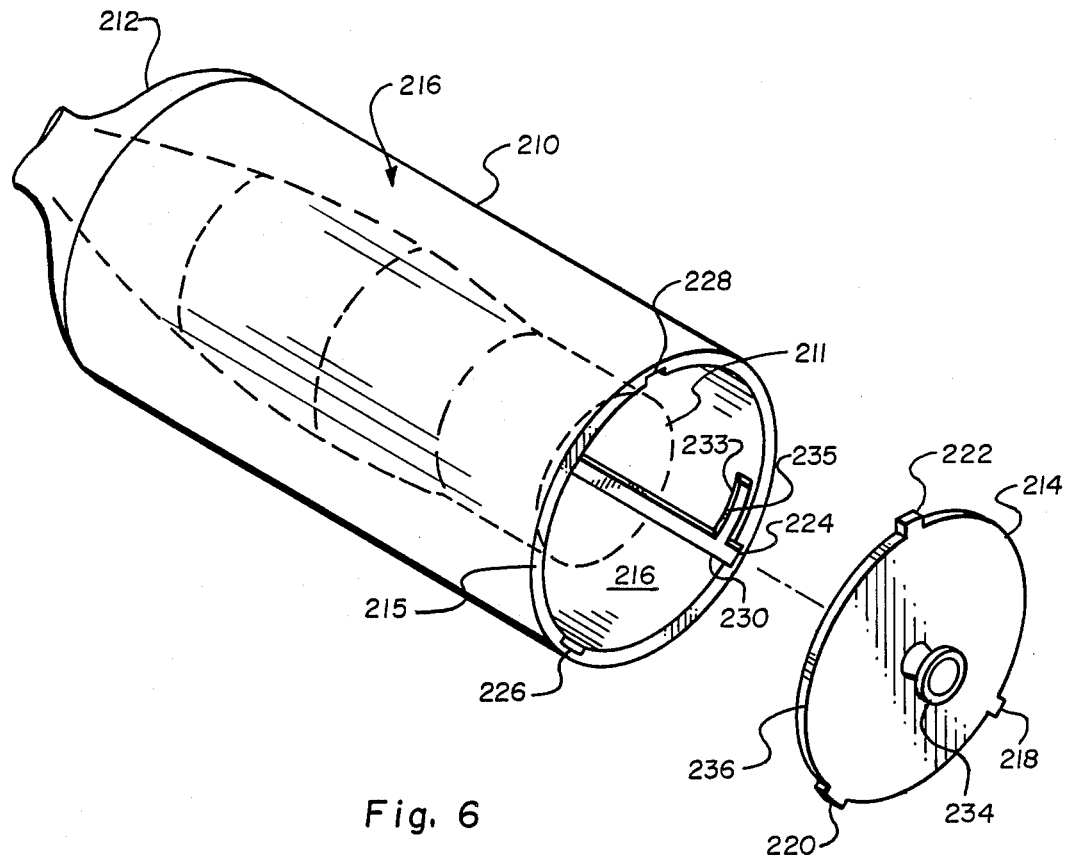
FIG. 6 is a perspective illustration of an actuator container of the instant invention.

Referring now to FIG. 6, an actuator container 210 is shown with reservoir means and more particularly a respiration bag 211 therewithin in dotted or phantom. The actuator container 210 here illustrated is cylindrically formed with a neck 212 configured to adapt to a valve such as valve 102 (FIG. 2) and valve 66 (FIG. 1) within a disposable breathing circuit. The container 210 may have a side such as bottom 214 sealably secured to the cylinder 215 so that inspiration signals can be supplied to the region 216 between the respiration bag 211 and the container 210 to cause the respiration bag 211 to move between its first position and its second position. The bottom 214 here shown has a plurality of lugs and more particularly three lugs 218, 220 and 222. The lugs are each positioned and sized to register with corresponding channels 224, 226 and 228. Near the distal end 230 of each channel 224, 226, and 228, a transverse channel 233 is formed and sized so that the end 214 may be rotated by handle 234 to cause the lugs 218, 222 and 220 to slide in their respective transverse channels 233. That is, lug 218 is inserted into the channel 224 and positioned and rotated into channel 233 to cause the lug 218 to be snugly secured. The channel 233 is formed with narrowing side walls 235 so that a friction fit can be obtained to snugly hold the bottom or side 214 in place. The bottom or side 214 may have an acceptable seal 236 to maintain an airtight seal within the container. Of course, a flexible bag such as that illustrated in FIGS. 1, 2 and 4 is preferable in that the user may squeeze it when manual operation is desired.

In operation, the user may manipulate the handle 234 to cause the side 214 to be urged inwardly towards the neck 212. The side 214 will therefore contact the respiration bag 211 therewithin so that it may be collapsed or squeezed.

The inward urging of side 214 and in turn of the bag 211 to a collapsed condition may be necessary in some circumstances, particularly in the event of a mechanical failure of other system components. It may also be desirable in those circumstances where the user would like to have a feel for the resistance. That is, upon pushing the side 214 toward the neck 212, the user will be able to obtain a feeling as to the pressure of respiratory gas being inserted via a breathing circuit into the patient's lungs and with experience to recognize excessive pressure to avoid damage to the patient's lungs.

Figure 7:
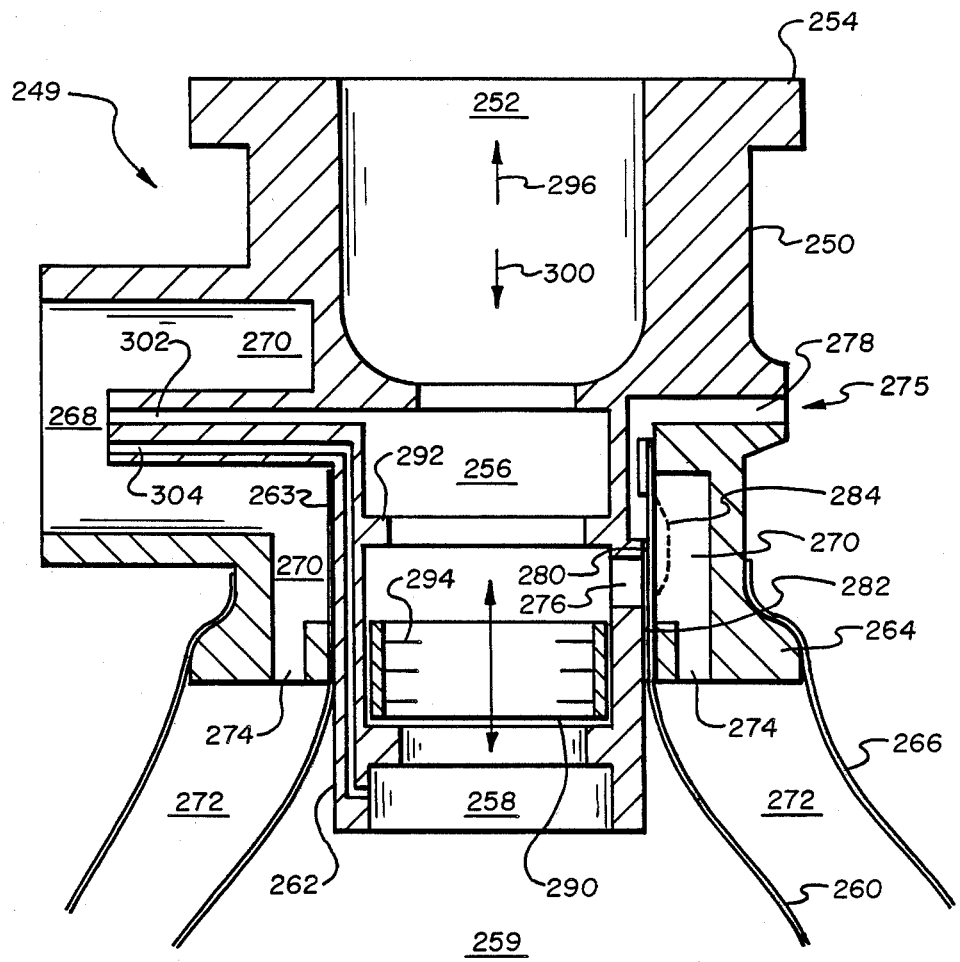
FIG. 7 is a cross-sectional representation of a valve for use in the systems of the instant invention.

Referring now to FIG. 7, a valve such as valve 66 (FIG. 1) and 102 (FIG. 2) is illustrated in cross section. The valve body 250 is formed with a first opening or port 252 to be in communication to receive and supply respiratory gas in a disposable breathing circuit such as depicted in FIG. 1. Desirably interconnecting tubing may be secured at and/or over or around an appropriate inner flange 254 provided for effecting the necessary connection in a conventional manner.

The first port 252 is in direct communication via channel 256 with a second port 258. The second port 258 is formed in the valve body 250 to be in communication with the reservoir means, and more particularly with the interior 259 of respiration bag 260 which is secured to the valve body 250 at and by respiration bag connecting means 262. The connecting means 262 is a cylindrical surface formed in the valve body 250 and sized to snugly receive the neck 263 of the respiration bag 260.

The valve of FIG. 7 also includes actuator connection means which is more particularly a flange structure 264 to facilitate attachment of actuation means to the valve body 250. As here illustrated, the actuation means is an actuation bag 266 which is snugly and elastically positioned over the flange 264. Alternately, it may be inelastic but secured by clamps (not shown) or other similar means as desired by the user.

The valve body 250 also has a third port 268 formed therein to receive inspiration and expiration signals from ventilation machine means and to supply them via channel 270 to the region 272 between the actuator bag 266 and the respiration bag 260 via a fourth port 274 formed in the valve body 250.

The valve of FIG. 7 preferably has a vent 275 formed therein positioned to vent gas from the first channel 256 to outside the valve body 250 when the pressure of the gas in the channel 256 exceeds a preselected pressure. The vent 275 is a third channel having a first portion 276 and a second portion 278. The neck 263 of the respiration bag 260 is positioned snugly at the surfaces 280 and 282 to be sealably positioned in the third channel between the first portion 276 and the second portion 278. The respiration bag 260 deforms to cause the formation of a deformation 284 shown in dotted line in FIG. 7 so that gas may proceed from the first portion 276 and into the second portion 278 of the channel. Notably, the gas pressure in the channel 270 is exerted against one side of the respiration bag 260 so that the pressure in the first portion 276 to cause deformation to the open position 284 will vary based on the pressure existing in channel 270. A high pressure in channel 270 will raise the pressure necessary to cause deformation to the second position 284.

The valve of FIG. 7 also includes a hollow slide gate 290 which is positioned in the first channel 256 to move between a first position, which precludes gas from communicating into the first portion 276 of the third channel, and a second position in which gas is communicated into the first portion 276 of the third channel. The slide gate 290 is hollow and sized to snugly and slidably fit within the channel 256. It is shown in FIG. 7 in the second position for free communication of gas between the first channel 256 and the first portion 276 of the third channel. In the first position, the slide gate 290 is position to abut ridge 292. A plurality of vanes, such as vane 294, are formed inside the slide gate so that gas flowing through gate 290 and the first channel 256 in an outward direction 296 will urge the slide gate 290 to the first position and, in turn, cause the gas within the respiration bag 260 to be communicated through channel 256, the first port 252, and into the tube means of its respective disposable breathing circuit. The inflow 300 of gas through gate 290 and past the vanes 294, urges the slide gate 290 to the second position as illustrated to expose the first portion 276 of the third channel so that venting may occur. Indeed, with a continuous supply of a preselected mixture of gas from an anesthesia machine, frequent venting may be necessary or may even be desirably preset by controlling the input flow of the preselected mixture of gas from an anesthesia machine.

The valve of FIG. 7 also desirably includes pressure sensing means which is here shown to be a first pressure sensing channel 302 and a second pressure sensing channel 304 formed in the valve body. Channel 302 senses pressure towards the first port 252, and channel 304 senses pressure towards the second port 258. Alternately, pressure transducers may be positioned to sense the pressure towards the first port and towards the second port to supply signals reflective of their pressures via conductors not here shown. The pressure differential is used to calculate flow rate in and out of the bag 260.

Referring to FIG. 8, the valve 249 of FIG. 7 is shown in perspective to show that the third port 268 is part of an overall connector structure 310 for connection to the ventilation machine. That is, the port 268 is to be connected to a connector such as connector 182 of FIG. 5. The pressure connectors communicate through a multi-lumen hose through their respective channels such as channel 312 (FIG. 5) to a differential pressure transducer 314 which sends an electric signal reflective of the differential pressure via conductor 316 to microprocessor 128 for display on the display panel 138 of the ventilation machine. FIG. 8 also clearly illustrates the vent port 318 to vent gas under pressure to atmosphere from the second portion 278 of the third channel.

FIG. 9 depicts a ventilation machine such as a ventilation machine of FIG. 5, the ventilation or ventilator machine 72 of FIG. 2, and the ventilation or ventilator machine 14 of FIG. 1. The ventilator 330 illustrated in FIG. 9 has a chassis 332 containing various components such as the components shown in FIG. 5. The display 138 is readily apparent and includes a pressure display portion 334, a volume display portion 336 and a rate display and control portion 338.

The pressure display portion 334 is here shown to have a plurality of LEDs (light-emitting diodes) 340 to illustrate the pressure of respiratory gas being supplied to the patient in centimeters of water. For example, the six lower LEDs are shown to be illuminated by illustrating them to be white in color and to, in turn, indicate a supply pressure to the patient of 20 centimeters of water. Other LEDs are present to show the existence of a patient trigger 342 where the patient will be breathing on his or her own as well as the presence of apnea or system disconnect 344.

The volume control section 336 also has an LED bar indicator 346 along with LED indication of tidal volume 348 (TV) or minute volume 350 (MV). In this illustration, the tidal volume is illustrated by showing it to be white and, in turn, showing a 0.5 liter tidal volume. A sliding bar structure 352 is shown with sliding contacts 353 and 354 so that alarm points may be set to indicate a tidal volume or minute volume which is too low or too high. That is, the user can slide adjustable contacts 353 and 354 along the bar 356 to select alarm points as desired based on the size of the patient. For example, a small child or teenager may certainly require a smaller tidal volume or minute volume than a large adult. Other arrangements may be used to select alarm points. However, the alarm points are desired so that the user may be alerted to the presence of an unsatisfactory or undesired condition. The volume can be adjusted up and down by operation of pressure switches 358 and 360 as desired.

Referring to the rate display and control panel 338, a bar indicator 361 shows the rate of respiration. A white illuminated LED next to the number 20 indicates a respiration rate of 20 breaths per minute. The respiration rate may be adjusted by manipulating the switches 362 and 364 to increase or decrease the respiration rate. Inspiration to expiration ratio is also shown to be selectable between 1 to 1, 1 to 2, and 1 to 3. The ratio of 1 to 1 is shown selected here because the LED 366 is shown to be illuminated or white. The inspiration to expiration ratio can be changed by manipulating the switches 368 and 370.

The chassis 330 also shows a battery indication panel 372 to show the state of charge of a battery associated with and acting as the power supply 374 (FIG. 5). A separate switch 376 is provided to silent audible alarms or to cause the alarms to be audible. A buzzer or bell is provided as necessary to act as the audible alarm and is part of the display circuitry. A mode control panel 378 is also shown having switches to select spontaneous 380 and controlled 382 operation. With the selection of spontaneous, the patient spontaneously breathes with assistance from the ventilation system into which the ventilation machine is connected. Similarly, the selection of controlled operation 382, all of the patient's breathing and respiration is controlled by the ventilation machine via a disposable breathing circuit associated with the particular system at hand. FIG. 9 also shows a manual inspiration switch 384 which may be operated to override the electrical components and cause the ventilation machine to fill the patient's lungs. The mode control panel 378 has appropriate LEDs 381 and 383 to illustrate the selected mode. The ventilator 330 of FIG. 9 also has a plug connector 386 for connection to an external source of power if desired.

Figure 10:
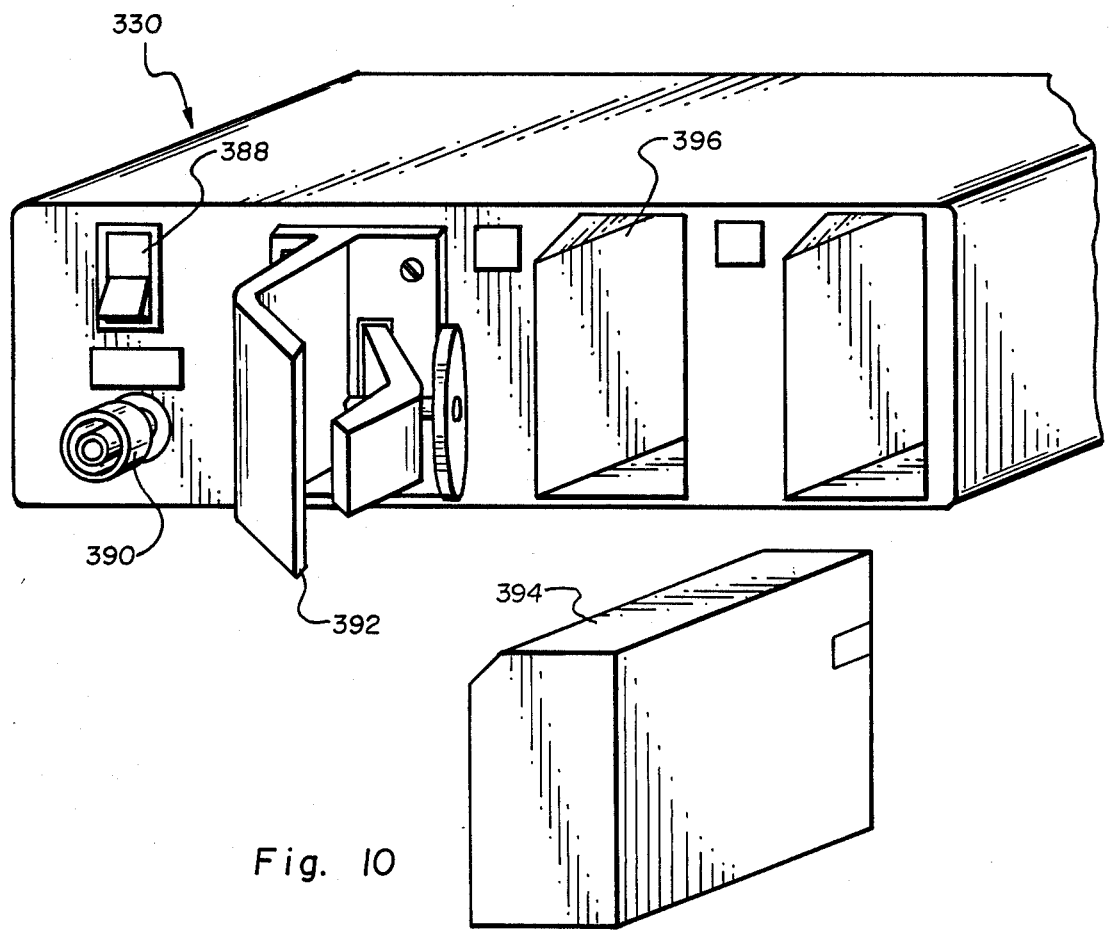
FIG. 10 is a rear view of the ventilation machine of FIG. 9.

FIG. 10 illustrates the rear view of the ventilator 330 of FIG. 9 and shows an on/off switch 388 as well as a connector 390 to act as the connector 182 (FIG. 5). A bracket structure 392 is shown to mount the ventilator machine 330 to an IV pole or similar structure (e.g., bed rail or gurney) available in a hospital environment for positioning proximate a patient. Also shown are two rechargeable battery packs 394 and 396. A nickel-cadmium rechargeable battery pack may be desired in order to facilitate the use of the ventilator 330 as a transport device and also to provide emergency backup in the event of lost power.

Figure 11:
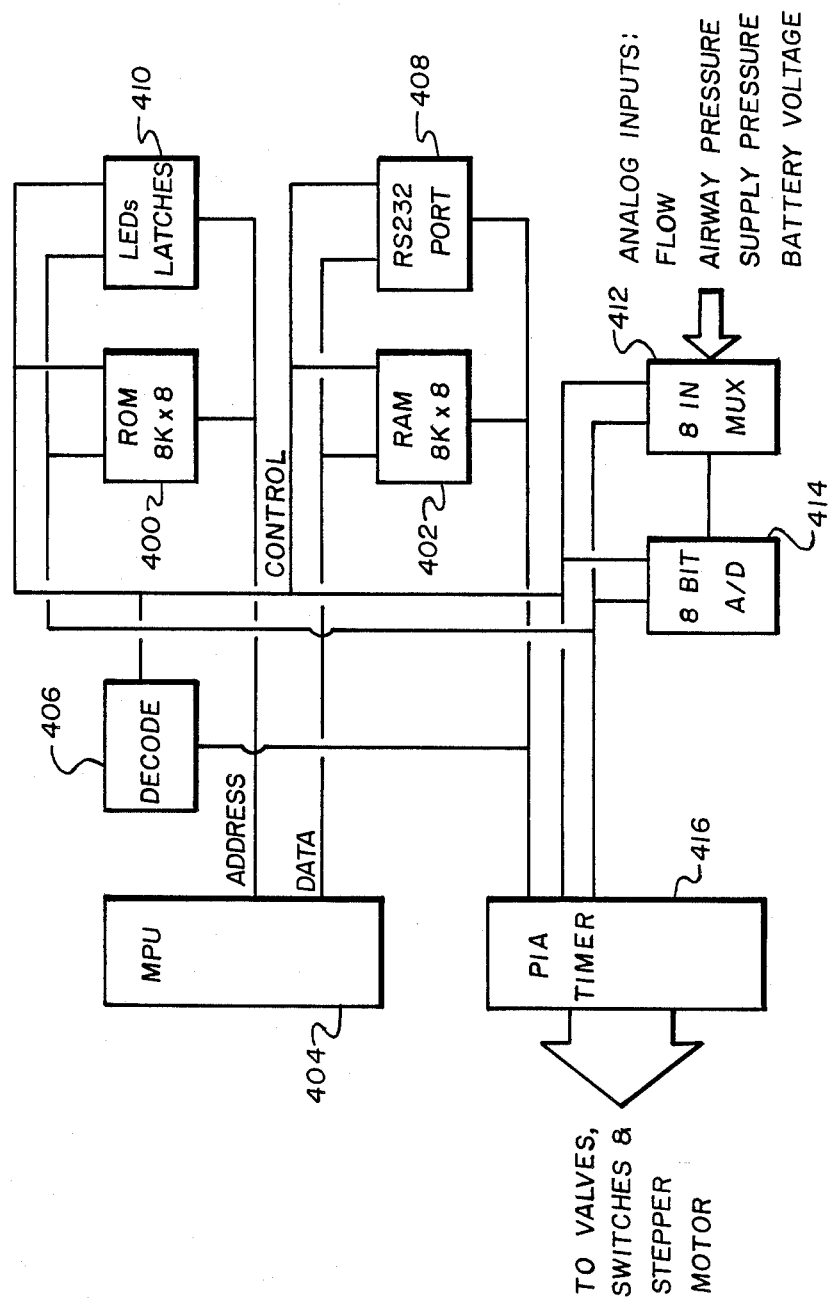
FIG. 11 is a block diagram of the components of the microprocessor system within the ventilation machine of the instant invention.

FIG. 11 shows a block diagram of the components of the microprocessor 128 of a ventilation machine of the type illustrated in FIGS. 9 and 10. Those skilled in the art will recognize that the circuitry there illustrated is based on a Motorola MC6809 microprocessor chip which includes the ROM 400, the RAM 402, the main power unit 404, the code and decode system 406, and the data port 408. In addition, the microprocessor chip here includes the light-emitting diode latches 410, multiplexer input circuitry 412, analog digital computer converter 414, and a timer 416 to supply pulsed control signals to the valves, switches and the stepper motor as hereinbefore discussed.

Figure 12:
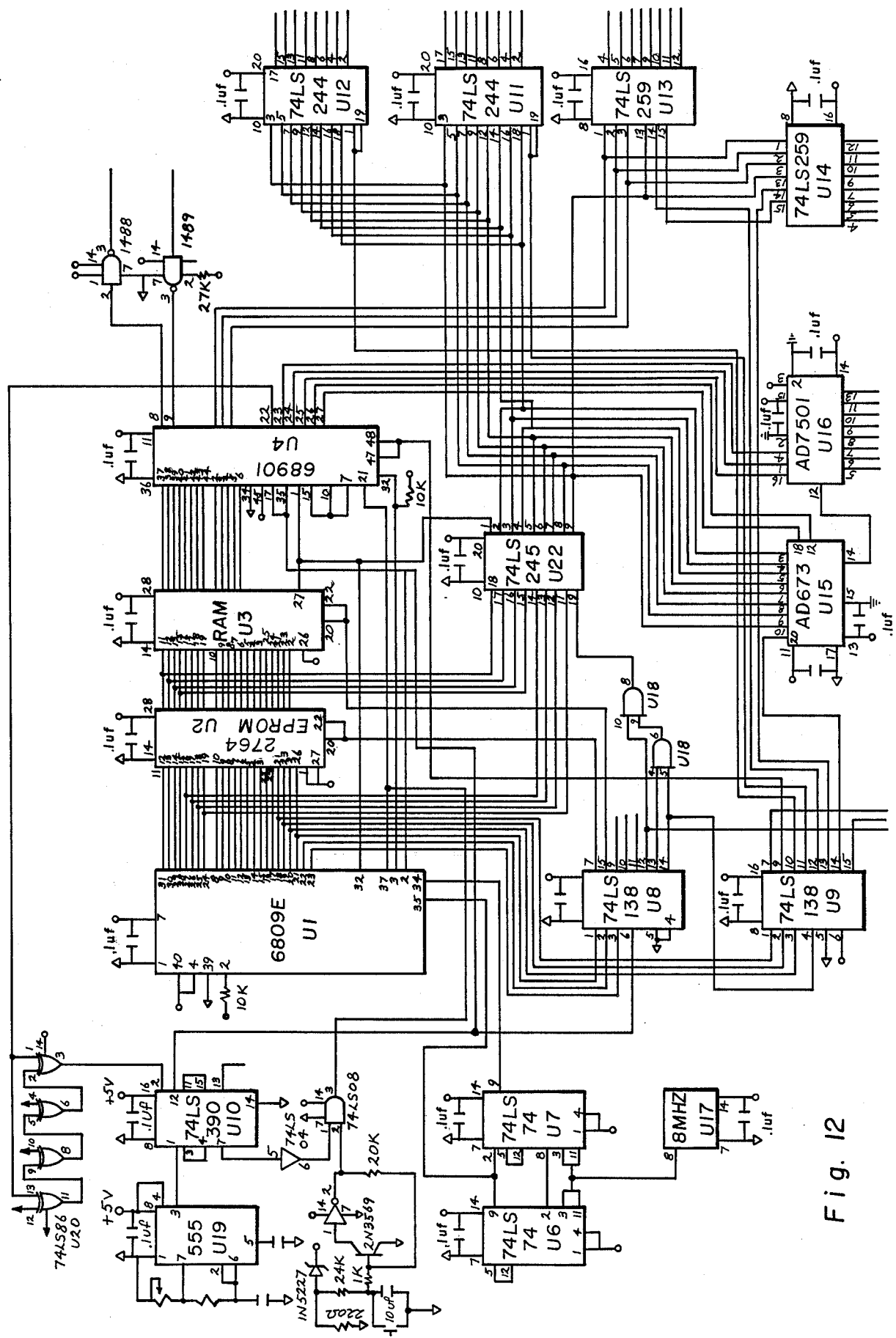
FIG. 12 is a circuit diagram of a microprocessor board for use within the microprocessor of the ventilation machine of the instant invention.

FIG. 12 is a detailed circuit diagram of a microprocessor board presently contemplated for use as the microprocessor of the ventilation machine such as the ventilation machine of FIGS. 5, 9 and 10 for use in the instant invention.

Figure 13:
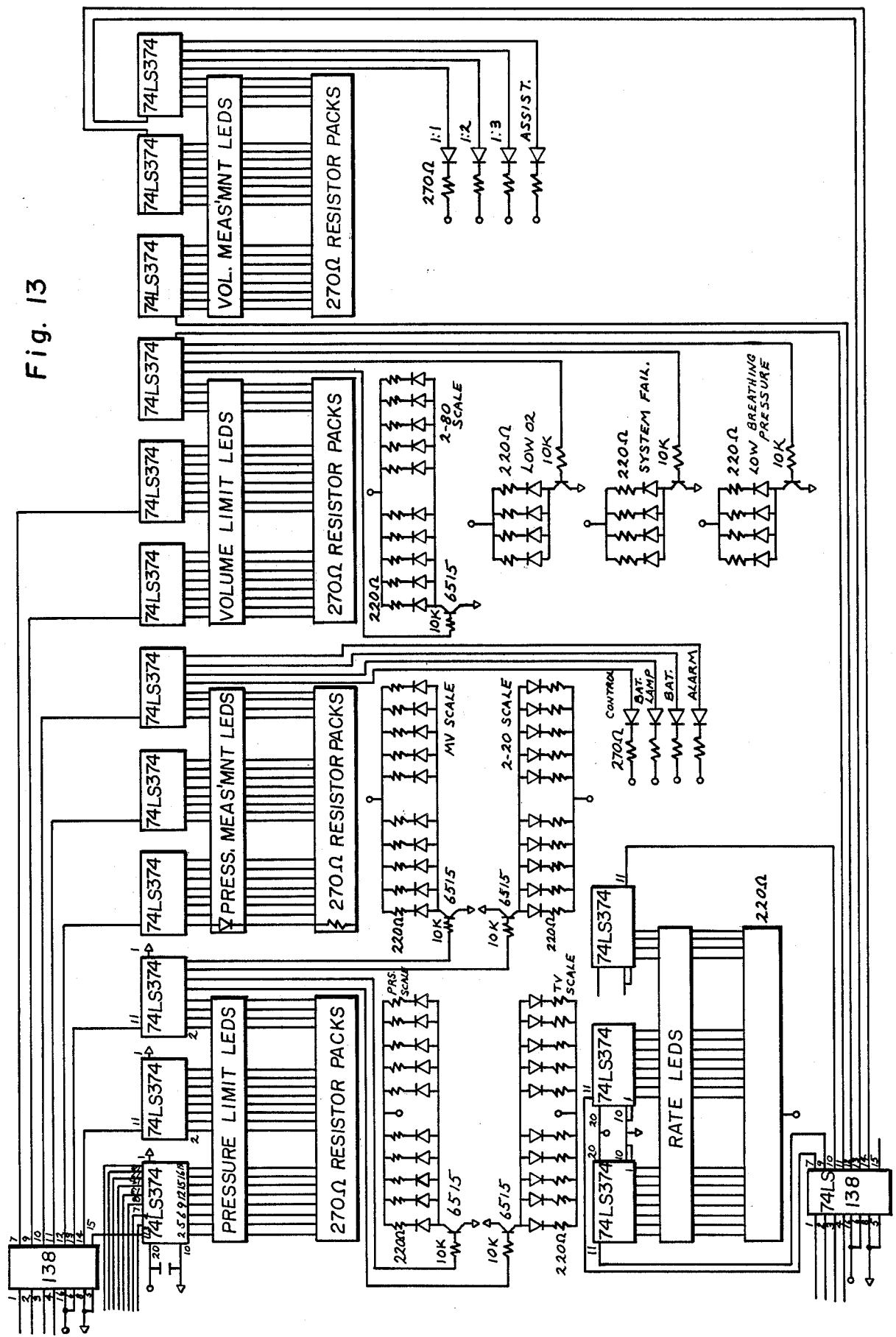
FIG. 13 is a circuit diagram of a display circuit board to operate the display circuitry of a ventilation machine of the instant invention.

FIG. 13 similarly is a detailed circuit diagram of the display circuit board, which in turn controls not only the display but also the control signal input of the ventilation machine such as the ventilation machine of FIG. 5, 9 and 10.

Figure 14:
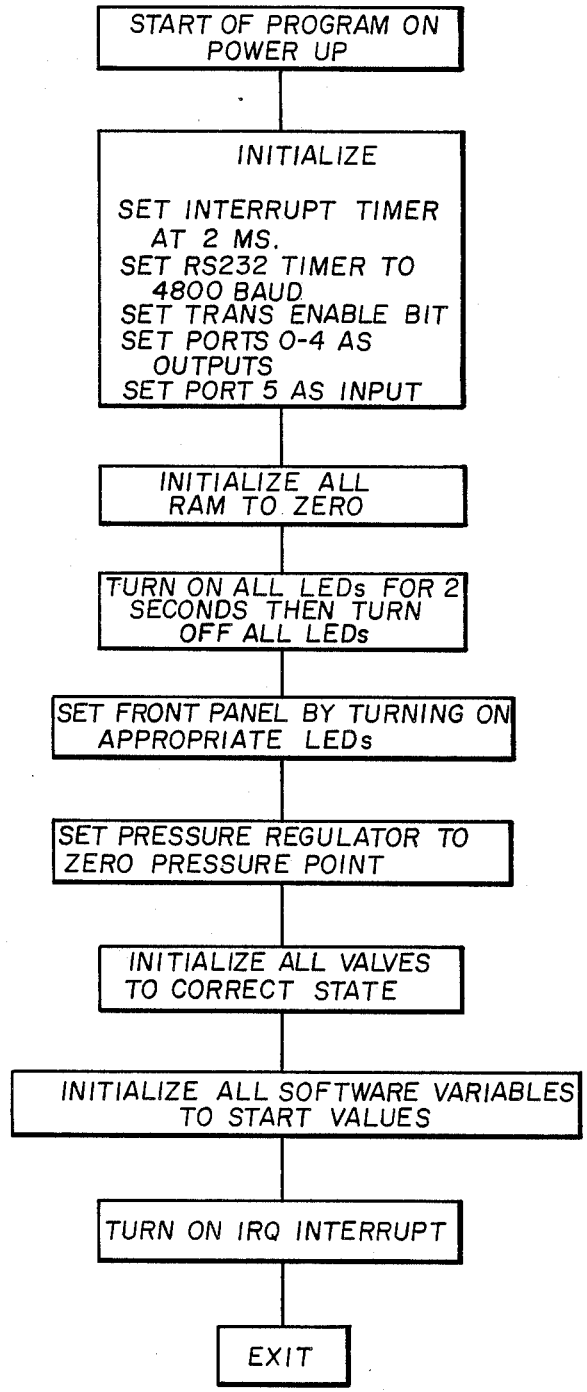
FIG. 14 is a block flow chart of the program used in the microprocessor of the ventilation machine of the instant invention.
Figure 15:
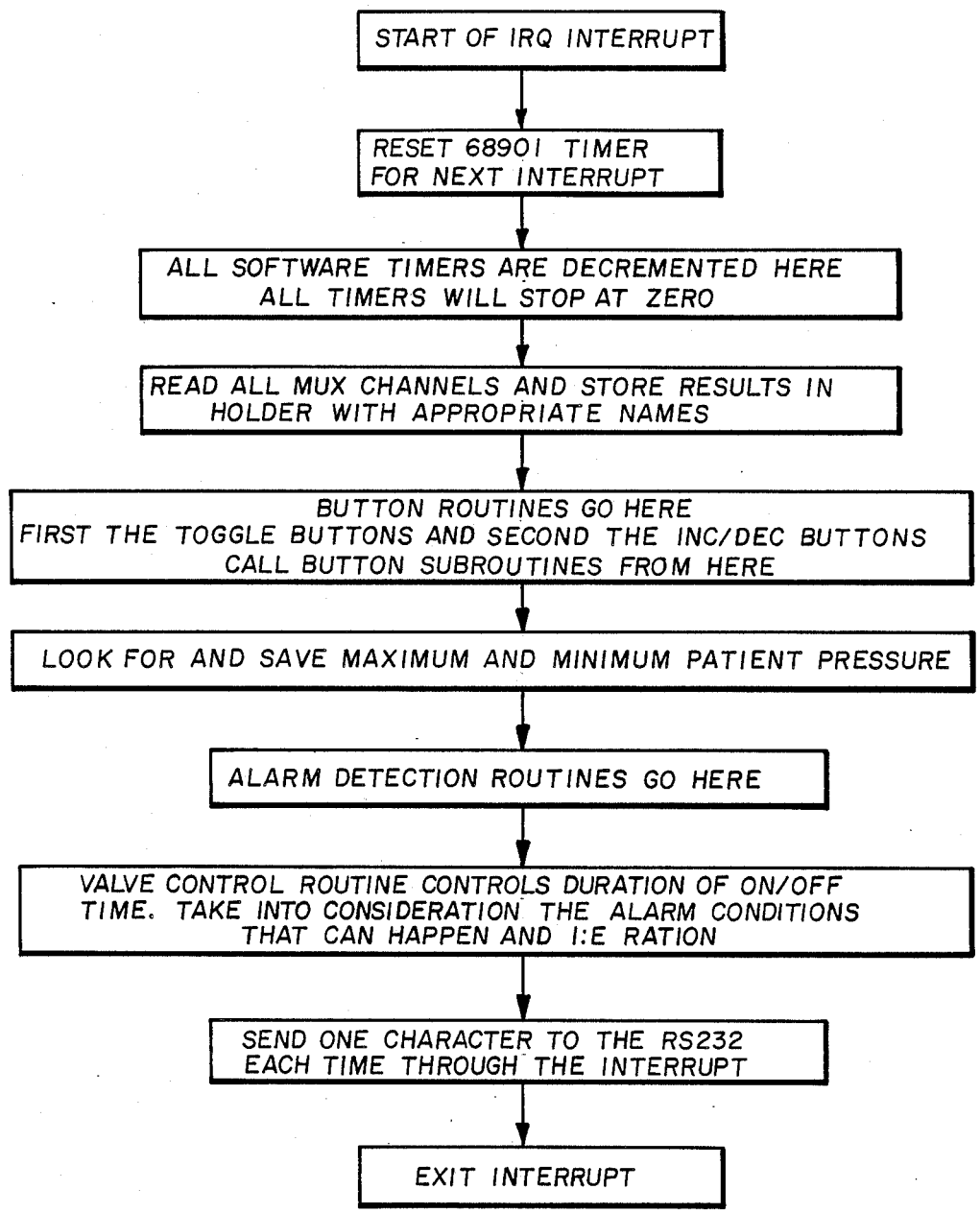
FIG. 15 is a continuation of the ventilator program of the microprocessor of the ventilation machine of the instant invention.
Figure 16:
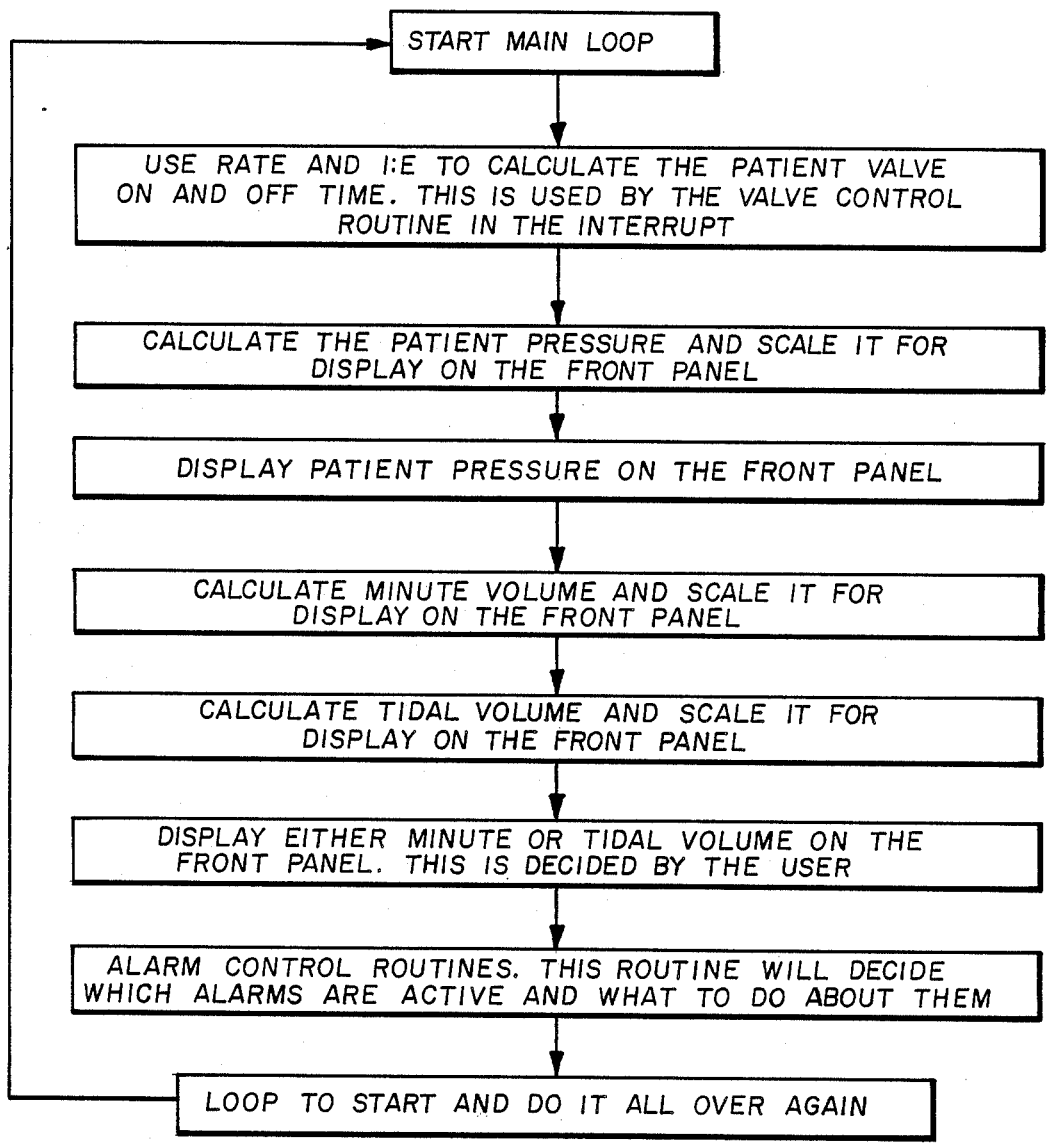
FIG. 16 is a continuation of the block diagram or flow chart of the program for use in the microprocessor of the ventilation machine of the instant invention.

FIGS. 14, 15 and 16 are the block flow chart of the program of the microprocessor 128 (FIG. 5) of a ventilation machine of the type used in the systems of the instant invention. Those skilled in the art will recognize the architecture of the program from which a particular program may be quickly and readily developed based on the individual desires of the user.

It should be appreciated that the systems herein disclosed provide for total isolation of the respiratory gas of the patient from the reusable components of the system. More particularly, the breathing circuits 12 and 70 of FIGS. 1 and 2 may be manufactured of relatively inexpensive materials to be readily disposable. The associated tubes and one-way valves may be made out of various types of plastics or synthetic materials at a relatively low cost. The pressures are relatively low so that slip fitting and similar low-cost configurations may be readily used in the assembly of the disposable breathing circuit for use in the particular system desired.

In order for the system to be disposable, isolation must be affected between the breathing circuit and a ventilation machine. The systems of the instant invention provide for such isolation by providing for a reservoir means or a respiration bag surrounded by an actuator. Pressure and negative pressure is used to collapse and expand the respiration bag and also to simultaneously isolate the ventilation machine from respiration or respiratory gas. Thus, the ventilation machine cannot be contaminated by respiration gas. Similarly, a positive supply of anesthesia gas or a preselected mixture of gas from an anesthesia machine or from another external source such as a blender precludes the flow of respiratory gas into the anesthesia machine and also in the blender. As a result, the anesthesia machine or the blender remains isolated from the patient since respiration gas cannot be communicated thereto.

In operation, an anesthesia system or a transportation ventilation system of the instant invention may be operated to totally isolate subsequent patients from contact with respirated organisms of a prior user by simply disposing of the disposable breathing circuit which is constructed of low-cost materials and is, in turn, low cost in relation to the risk of communicating a serious disease. For example, bronchial diseases are readily communicated by oral means along with many other well-known diseases. Heretofore no effort has been made to isolate the breathing circuits from the anesthesia machine or the ventilation machine or to provide a ventilation machine which is small, compact and highly portable but at the same time isolated from the disposable breathing circuit.

It is to be understood that the embodiments of the invention above described are merely illustrative of the application of the principles of the invention. Reference herein to details of the illustrated embodiments is not intended to limit the scope of the claims, which themselves recite those features regarded as essential to the invention.

We claim:
1. An anesthesia system comprising:
   anesthesia machine means connected to an external gas source to receive gas therefrom, and connected to continuously supply a preselected mixture of gas, said anesthesia machine means have means to mix the gas received into said preselected mixture of gas;
   a disposable breathing circuit interconnectable between said anesthesia machine means and a patient, said disposable breathing circuit having:
      first connector means for connection to said anesthesia machine means to receive said preselected mixture of gas therefrom,
      second connector means for connection to said patient to supply and receive respiratory gas,
      reservoir means connected for receiving, storing and supplying said preselected mixture of gas and for receiving, storing and supplying said respiratory gas and for adding said preselected mixture of gas thereto, tube means interconnected between said first connector means, second connector means and said reservoir means to communicate said respiratory gas from said patient to said reservoir means upon expiration of gas from said patient and from said reservoir means to said patient upon inspiration of gas to said patient, and to communicate said preselected mixture of gas from said anesthesia machine means to said reservoir means, actuator means positioned operatively proximate to said reservoir means to urge said reservoir means between a collapsed first position in which said preselected mixture of gas and respiratory gas therewithin are supplied from said reservoir means to the patient via said tube means and an expanded second position in which the respiratory gas is expelled from the patient via said tube means and to receive said preselected mixture of gas via said tube means from said anesthesia machine means;

excessive gas pressure relief means in communication with said respiratory gas and said preselected mixture of gas during all but the time said gases are being supplied from said reservoir means to the patient; and means operated by the flow of gases from the reservoir means to the patient for blocking communication of the excessive gas pressure relief means with the respiratory gas and the preselected mixture of gas during supply of said gases to the patient; and ventilation machine means for generating inspiration signals and expiration signals in accordance with a preselected pattern and removably connected to said actuator means to supply said inspiration signals and expiration signals thereto for urging said reservoir means between said first and second positions respectively.

2. The anesthesia system of claim 1 wherein said reservoir means is a respiration bag which is formed to collapse upon receipt of said inspiration signals and expand upon receipt of said expiration signals.

3. The anesthesia system of claim 2 wherein said actuator means includes an actuation container formed of a substantially inelastic material, wherein said respiration bag is sealably positioned within said actuation container, and wherein said inspiration signals are a positive pressure signal to urge said respiration bag to said first collapsed position and said expiration signals are the absence of positive pressure signals so that said respiration bag may be urged to said second expanded position.

4. The anesthesia system of claim 3 wherein said actuation container is a rigid container with sides, one of which is manually and slidably movable toward the interior of said rigid container to contact and collapse said respiration bag.

5. The anesthesia system of claim 2 wherein said actuator means includes an actuator bag formed of a gas impermeable and substantially inelastic flexible material to be manually collapsible about said respiration bag.

6. The anesthesia system of claim 5 wherein said disposable breathing circuit further includes absorber means interconnected to receive the respiratory gas from the patient and to supply the respiratory gas to said respiration bag, said absorber means operating to remove carbon dioxide from the respiratory gas.

7. The anesthesia system of claim 6 wherein said second connector is a Y connector having a first leg for connection to the patient, a second leg for transmission of the respiratory gas, and a third leg for receipt of the respiratory gas, wherein said tube means includes a first branch interconnected between said second leg and said absorber means, a second branch interconnected between said first branch and said anesthesia machine means, a third branch interconnected between said absorber means and said respiration bag, and a fourth branch interconnected between said third branch and said third leg, said first branch further including a one-way valve positioned and operative for communicating respiratory gas from the patient and inhibiting the flow of gas therethrough to the patient, and said fourth branch further including a one-way valve positioned and operative for communicating respiratory gas to the patient and inhibiting the flow of respiratory gas from the patient.

8. The anesthesia system of claim 7 wherein said second branch includes a third one-way valve interconnected for communicating the preselected mixture of gas therethrough from said anesthesia machine means and inhibiting the flow of gas to said anesthesia machine means.

9. The anesthesia system of claim 8 wherein said fourth branch includes oxygen sensor means interconnected to sense oxygen concentration of the respiratory gas and generate signals reflective thereof to a remote indicator.

10. The anesthesia system of claim 9 wherein the anesthesia machine means receives a supply of oxygen and gas anesthetic from the external source, includes means to adjustably mix the oxygen and gas anesthetic and to supply same at a pressure preselected to cause flow.

11. The anesthesia system of claim 10 wherein the ventilator machine means is connected to an external source of gas and includes:
  power supply means to supply power;
  valve means interconnected to receive gas from the external source of gas for opening and closing in accordance with open and close signals to supply and to restrict the flow of the gas;
  signal generation means to generate open and close signals in accordance with a preselected pattern; and
  output means connected to said valve means and to said actuator means to communicate the gas as said inspiration and expiration signals.

12. The anesthesia system of claim 5 wherein said actuator means further includes a valve to interconnect said respiration bag with said tube means and to interconnect said actuator bag to said ventilation machine means, said valve having:
  a valve body;
  a first port formed in said valve body for connection to said tube means to communicate gas therebetween;
  respiration bag connection means associated with said valve body for sealed connection of said respiration bag thereto;
  a second port formed in said valve body positioned and connected to said respiration bag to communicate gas therebetween a channel formed in said valve body to intercommunicate gas between said first port and said second port;

actuator connection means associated with said valve body for sealed connection of said actuator bag for intermittently actuating said respiratory bag;

third port means formed in said valve body for interconnection to said ventilation machine means;

fourth port means formed in said valve body positioned and connected to said actuator bag to communicate inspiration and expiration signals thereto from said ventilation machine means; and second channel means formed in said valve body to intercommunicate said expiration and inspiration signals between said third port means and said fourth port means.

13. The anesthesia system of claim 12 wherein the excessive gas pressure relief means includes vent means formed and positioned to vent gas from said first channel to outside the said valve body when the pressure of the gas exceeds a preselected pressure.

14. The anesthesia system of claim 13 wherein said vent means includes a third channel having a first and second portion formed in said valve body, wherein said respiration bag has a vent portion sealably positioned in said channel between said first and second portion, said respiration bag being deformable at said preselected pressure to communicate gas from said first portion to said second portion.

15. The anesthesia system of claim 13 wherein the means operated by the flow of gases from the reservoir means to the patient for blocking communication of the excessive gas pressure relief means includes a slide gate positioned in said first channel and movable from a first, normal position in which gas is communicated into said channel, to a second position to preclude gas from communication into said third channel during flow of gases in the first channel from the reservoir to the patient.

16. The anesthesia system of claim 15 further including a first pressure sensing means formed and positioned within said valve body to sense pressure in said first channel between said first port and said slide gate, and a second pressure sensing means positioned and formed in said valve body to sense pressure in said first channel between said second port and said slide gate, whereby the flow rate of gases through the first channel may be determined based on the difference in pressure measured by the first and second pressure sensing means.

17. The anesthesia system of claim 2 wherein said ventilation machine means includes:

first connector means for connection to an external source of pressurized gas at a supply pressure;

pressure regulator means connected to receive the pressurized gas from said first connector means and to supply regulated gas, said pressure regulator means having means to control the pressure of the pressurized gas to be regulated gas at pressures at and below the supply pressure, as selected by the user;

signal valve means connected to receive the regulated gas and to open and close in accordance with a preselected pattern to supply said inspiration signals when open and expiration signals when closed; and second connector means for connecting the signal valve means to said actuator means.

18. The anesthesia system of claim 17 wherein said ventilation machine means further includes:

mixing means interconnected to receive the regulated gas from said signal valve means, said mixing means having means to receive gas from a second source and mix the gas from said second source with the regulated gas to form signal gas; and check and vent means connected to receive and communicate the signal gas from said mixing means to said second connector means, to inhibit the flow of gas from said second connector means into said mixing means to the vent gas from said second connector means when said signal valve means is closed.

19. The anesthesia system of claim 18 wherein said pressure regulator means is electrically controlled and wherein said signal valve means is an electrical solenoid valve, wherein said ventilation machine means includes sensing means to sense pressure parameters, input means to select desired parameters and output means to supply control signals to said pressure regulator and electrical solenoid valve for operation thereof as selected by the user.

20. A disposable breathing circuit comprising:

first connector means for connection to a continuous supply of breathable gas;

second connector means for connection to a patient to supply and receive respiratory gas;

reservoir means connected for receiving, storing and supply the breathable gas and for receiving, storing and supplying the respiratory gas and for adding the breathable gas therewith;

tube means interconnected between said first connector means, said second connector means, and said reservoir means to communicate the respiratory gas from the patient and to said reservoir means and from said reservoir means to the patient, and to communicate the breathable gas from said first connector means to said reservoir means;

actuator means positioned operatively proximate to said reservoir means to urge said reservoir means between a first collapsed position in which the breathable gas and respiratory gas therewithin are supplied from said reservoir to the patient via said tube means, and a second expanded position to receive the respiratory gas from the patient via said tube means and to receive the breathable gas via said tube means from said first connector means, said actuator means being connected to an external source of inspiration and expiration signals to urge said reservoir means between said first and second positions respectively;

low pressure relief means in communication with the respiratory and the breathable gases during all but the time the gases are being supplied from the reservoir means to the patient; and means operated by the flow of gases from the reservoir means to the patient for blocking communication of the low pressure relief means with the respiratory and breathable gases during supply of the gases to the patient.

21. The disposable breathing circuit of claim 20 wherein said reservoir means is a respiration bag which is formed to collapse upon receipt of said inspiration signals and expand upon receipt of said expiration signals.

22. The disposable breathing circuit of claim 21 wherein said actuator means includes an actuation container formed of a substantially inelastic material, wherein said respiration bag is positioned within said actuation container, and wherein said inspiration signals are a positive pressure signal to urge said respiration bag to said first collapsed position and said expiration signals are the absence of pressure signals so that said respiration bag may be urged to said second expanded position.

23. The disposable breathing circuit of claim 22 wherein said actuation container is a rigid container w sides, one of which is manually and slidably movable toward the interior of said rigid container to contact and collapse said respiration bag.

24. The disposable breathing circuit of claim 21 wherein said actuator means includes a bag formed of a gas impermeable flexible material to be manually collapsible about said respiration bag.

25. The disposable breathing circuit of claim 24 further including absorber means interconnected to receive respiratory gas from the patient and to supply the respiratory gas to said respiration bag, said absorber means operating to remove carbon dioxide from the respiratory gas.

26. The disposable breathing circuit of claim 25 wherein said second connector is a Y connector having a first leg for connection to the patient, a second leg for transmission of respiratory gas, and a third leg for receipt of respiratory gas, wherein the tube means includes a first branch interconnected between said second leg and said absorber means, a second branch interconnected between said first branch and said first connector means, a third branch interconnected between said absorber means and said respiration bag, and a fourth branch interconnected between said third branch and said third leg, said first branch further including a one-way valve positioned and operative for communicating respiratory gas from the patient and inhibiting the flow of gas therethrough to the patient, and said fourth branch further including a one-way valve positioned and operative for communicating respiratory gas to the patient and inhibiting the flow of respiratory gas from the patient.

27. The disposable breathing circuit of claim 26 wherein said second branch includes a third one-way valve interconnected for communicating the anesthetic gas therethrough from said first connector means and inhibiting the flow of anesthetic gas to said first connector means.

28. The disposable breathing circuit of claim 27 wherein said fourth branch includes oxygen sensor means to sense oxygen concentration and generate signals reflective thereof to a remote indicator.

29. The disposable breathing circuit of claim 20 wherein said actuator means further includes a valve to interconnect said respiration bag with said tube means and to interconnect said actuator bag to said ventilation machine means, said valve having:
a valve body;
a first port formed in said valve body for connection to said tube means to communicate gas therebetween;
respiration bag connection means associated with said valve body for sealed connection of said respiration bag thereto;
a second port formed in said valve body positioned and connected to said respiration bag to communicate gas therebetween;
a channel formed in said valve body to intercommunicate gas between said first port and said second port;
actuator connection means associated with said valve body for sealed connection of said actuator bag for intermittently actuating said respiratory bag;
third port means formed in said valve body for interconnection to said ventilation machine means;
fourth port means formed in said valve body positioned and connected to said actuator bag to communicate inspiration and expiration signals thereto from said ventilation machine means; and
second channel means formed in said valve body to intercommunicate said expiration and inspiration signals between said third port means and said fourth port means.

30. The disposable breathing circuit of claim 29 wherein the excessive gas pressure relief means includes vent means formed and positioned to vent gas from said first channel to outside the said valve body when the pressure of the gas exceeds a preselected pressure.

31. The disposable breathing circuit of claim 30 wherein said vent means includes a third channel having a first and second portion formed in said valve body, wherein said respiration bag has a vent portion sealably positioned in said channel between said first and second portion, said respiration bag being deformable at said preselected pressure to communicate gas from said first portion to said second portion.

32. The disposable breathing circuit of claim 30 wherein the means operated by the flow of gases from the reservoir means to the patient for blocking communication of the excessive gas pressure relief means includes a slide gate positioned in said first channel and movable from a first, normal position in which gas is communicated into said channel, to a second position to preclude gas from communication into said third channel during flow of gases in the first channel from the reservoir to the patient.

33. The disposable breathing circuit of claim 32 further including a first pressure sensing means formed and positioned within said valve body to sense pressure in said first channel between said first port and said slide gate, and a second pressure sensing means positioned and formed in said valve body to sense pressure in said first channel between said second port and said slide gate, whereby the flow rate of gases through the first channel may be determined based on the difference in pressure measured by the first and second pressure sensing means.

34. A transport ventilation system comprising: a disposable breathing circuit having:
connector means for connection to a patient to supply and receive respiratory gas,
reservoir means connected to receive, store and supply said respiratory gas,
tube means connected to said connector means and said reservoir means to communicate the respiratory gas between the patient and said reservoir means,
supply means selectively adapted to said tube means and reservoir means to supply a breathable gas from an external source,
exhaust means interconnected in said tube means to exhaust respiratory gas from the patient,
actuator means positioned operatively proximate to said reservoir means to urge said reservoir means between a first collapsed position in which the breathable gas and the respiratory gas therewithin are supplied from said reservoir to the patient via said tube means, and a second expanded position to exhaust the respiratory gas from the patient via said connector means, said tube means, and said exhaust means and to receive said breathable gas via said tube means from said supply means;

excessive gas pressure relief means in communication with the respiratory and the breathable gases during all but the time the gases are being supplied from the reservoir means to the patient;

means operated by the flow of gases from the reservoir means to the patient for blocking communication of the excessive gas pressure relief means with the respiratory and breathable gases during supply of the gases to the patient; and ventilation machine means for generating inspiration signals and expiration signals in accordance with a preselected pattern and removably connectable to said actuator means to supply said inspiration signals and expiration signals thereto for urging said reservoir means between said first and second positions respectively.

35. The transport ventilation system of claim 34 wherein said reservoir means is a respiration bag which is formed to collapse upon receipt of said inspiration signals and expand upon receipt of said expiration signals.

36. The transport ventilation system of claim 35 wherein said actuator means includes an actuator bag formed of a gas impermeable flexible material to be manually collapsible about said respiration bag.

37. The transport ventilation system of claim 36 wherein said connector is a Y connector having a first leg for connection to the patient, a second leg for connection to said exhaust means, and a third leg for receipt of respiratory gas, wherein the tube means includes a first branch interconnected between said second leg and said exhaust means, a second branch interconnected between said third leg and said respiration bag;

said second branch further including a one-way valve positioned and operative for communicating respiratory gas to said patient and precluding communication of gas therethrough from the patient.

38. The transport ventilation system of claim 36 wherein said supply means includes an inlet one-way valve interconnected to supply air at atmospheric pressure.

39. The transport ventilation system of claim 36 wherein said supply means is a poppet valve structure positioned on said respiratory bag and extending through said actuator bag to supply air to said respiratory bag in operation between said first and second positions.

40. The transport ventilation system of claim 36 wherein said supply means includes a blender machine interconnected into said tube means to supply breathable gas under pressure.

41. The transport ventilation system of claim 40 wherein said exhaust means is a two-way valve having a first port connected to the patient to receive and supply respiratory gas, a second port open to the atmosphere to exhaust respiratory gas and a third port connected to said respiration bag via said tube means, said two-way valve being operable between a first position interconnecting said first port and said second port and a second position interconnecting said first port with said third port, said two-way valve moving between said first and second positions upon expiration and inspiration of the patient.

42. The transport ventilation system of claim 41 wherein said actuator means further includes:
a valve body;
a first port formed in said valve body connectable to a breathing circuit to communicate gas therebetween;
a respiration bag connector associated with said valve body for sealed connection of a respiration bag thereto;
a second port formed in said valve body positioned and connected to said respiration bag to communicate gas therebetween;
a channel formed in said valve body to intercommunicate gas between said first port and said second port;
actuator connection means associated with said valve body for sealed connection thereto of actuator means for intermittently actuating said respiratory bag;
third port means formed in said valve body for interconnection to an external source of actuation signals;
fourth port means formed in aid valve body positioned and connectable to said actuator means to communicate said actuation signals thereto; and
second channel means formed in said valve body to intercommunicate said actuation signals between said third port means and said fourth port means.

43. The transport means of claim 42 wherein said ventilation machine means includes:
first connector means for connection to an external source of pressurized gas at a supply pressure;
pressure regulator means connected to receive the pressurized gas from said first connector means and to supply regulated gas, said pressure regulator means having means to control the pressure of the pressurized gas to be regulated gas at pressures at and below the supply pressure, as selected by the user;
signal valve means connected to receive the regulated gas and to open and close in accordance with a preselected pattern to supply said inspiration signals when open and expiration signals when closed; and
second connector means for connecting the signal valve means to said actuator means.

44. The transport ventilation system of claim 43 wherein said ventilation machine means further includes:
mixing means interconnected to receive the regulated gas from said signal valve means, said mixing means having means to receive gas from a second source and mix the gas from said second source with the regulated gas to form signal gas; and
check and vent means connected to receive and communicate the signal gas from said mixing means to said second connector means, to inhibit the flow of gas from said second connector means into said mixing means to the vent gas from said second connector means when said signal valve means is closed.

45. The transport ventilation system of claim 42 wherein the excessive gas pressure relief means includes vent means formed and positioned to vent gas from said first channel to outside the said valve body when the pressure of the gas exceeds a preselected pressure.

46. The transport ventilation system of claim 45 wherein said vent means includes a third channel having a first and second portion formed in said valve body, wherein said respiration bag has a vent portion sealably positioned in said channel between said first and second portion, said respiration bag being deformable at said preselected pressure to communicate gas from said first portion to said second portion.

47. The transport ventilation system of claim 45 wherein the means operated by the flow of gases from the reservoir means to the patient for blocking communication of the excessive gas pressure relief means includes a slide gate positioned in said first channel and movable from a first, normal position in which gas is communicated into said channel, to a second position to preclude gas from communication into said third channel during flow of gases in the first channel from the reservoir to the patient.

48. The transport ventilation system of claim 47 further including a first pressure sensing means formed and positioned within said valve body to sense pressure in said first channel between said first port and said slide gate, and a second pressure sensing means positioned and formed in said valve body to sense pressure in said first channel between said second port and said slide gate, whereby the flow rate of gases through the first channel may be determined based on the difference in pressure measured by the first and second pressure sensing means.

* * * * *